United States Patent [19]

Crawford et al.

[11] Patent Number: 4,490,353
[45] Date of Patent: Dec. 25, 1984

[54] ANTIPLAQUE DENTIFRICE WITH IMPROVED FLUORIDE STABILITY

[75] Inventors: Richard J. Crawford, Asbury; Kathleen M. Yuhasz, Fords; John P. Curtis, Glen Gardner, all of N.J.

[73] Assignee: Colgate-Palmolive Company, New York, N.Y.

[21] Appl. No.: 513,474

[22] Filed: Jul. 13, 1983

[51] Int. Cl.$^3$ .......................... A61K 7/16; A61K 7/18; A61K 7/22
[52] U.S. Cl. ........................... 424/52; 424/49; 424/54; 424/57
[58] Field of Search ..................... 424/49–58

[56] References Cited

U.S. PATENT DOCUMENTS

| | | | |
|---|---|---|---|
| 3,927,201 | 12/1975 | Baines et al. | 424/54 |
| 3,937,805 | 2/1976 | Harrison | 424/54 |
| 4,025,616 | 5/1977 | Haefele | 424/54 |
| 4,036,950 | 7/1977 | Baines et al. | 424/54 |
| 4,059,624 | 11/1977 | Harrison | 424/54 |
| 4,067,962 | 1/1978 | Juneja | 424/54 |
| 4,098,878 | 7/1978 | Baines et al. | 424/49 |
| 4,123,517 | 10/1978 | Baines et al. | 424/54 |
| 4,198,392 | 4/1980 | Juneja | 424/54 |
| 4,282,204 | 8/1981 | Phillips et al. | 424/49 |
| 4,363,795 | 12/1982 | Wahlstam | 424/54 |

*Primary Examiner*—Shep K. Rose
*Attorney, Agent, or Firm*—Robert L. Stone; Murray M. Grill; Herbert S. Sylvester

[57] ABSTRACT

A stable antiplaque dentifrice with improved foaming and improved fluoride stability containing an antiplaque quaternary ammonium compound, a betaine surfactant to improve foaming without inactivating the anti-bacterial and antiplaque activity of the quaternary ammonium compound, a humectant selected from the group consisting of polyethylene glycol, sorbitol, and mixtures thereof, a nonionic gelling agent, preferably hydroxyethylcellulose and a fluorine-containing compound capable of providing a fluoride ion, a small amount of glycerin to improve fluoride stability in polyethylene glycol humectant, in an aqueous vehicle containing a dental abrasive. A small amount of glycerin, as low as 1%, improves the long term fluoride stability of the dentifrice without adversely affecting the cosmetic stability thereof.

17 Claims, No Drawings

ANTIPLAQUE DENTIFRICE WITH IMPROVED FLUORIDE STABILITY

BACKGROUND AND PRIOR ART

The present invention relates to an antiplaque dentifrice containing a quaternary active ingredient and at least 1.5% and up to 2% betaine surfactant by weight, such as cocoamidopropylbetaine, lauramidopropylbetaine, cocobetaine, etc., which enhances foaming and does not inactivate the antibacterial activity of the quaternary compound. Nonionic surfactants fail to afford sufficient foaming, and anionic surfactants inactivate the quaternary antibacterial activity. Carbowax 600 (polyethylene glycol), and/or sorbitol replace propylene glycol and glycerin as humectant in order to afford stability to the betaine-containing composition. Also, carboxymethyl cellulose is preferably avoided because large organic molecules deactivate the quaternary compound. Nonionic gums such as hydroxyethylcellulose is used as gelling/thickening agent for the dental cream. Another essential ingredient of this dentifrice is a fluorine-containing compound capable of providing a fluoride ion. More specifically, this composition is free of anionic and nonionic surfactants, and contains only a minimal amount of glycerin, 1-10%, and preferably 5-7% by weight, as a fluoride stabilizer.

It has been found that the addition of a betaine surfactant to an antiplaque dental formulation based on quaternary active ingredients, improves the foaming characteristics thereof, without deactivating the quaternary antimicrobial activity. It has additionally been found that humectants such as polyethylene glycol and/or sorbitol are required in the betaine system to effect cosmetic stability, and that the gelling/thickening agent be limited to nonionic gums such as hydroxyethylcellulose.

In a copending patent application, filed of even date, is described a cosmetically stable antiplaque dentifrice based on polyethylene glycol and/or sorbitol completely replacing glycerin as the humectant. Accelerated aging studies have shown the fluoride stability in this dentifrice to be marginal but acceptable.

It has been found that incorporating small amounts of glycerin, up to a maximum of 10%, into the fluoride-containing formulation, markedly improves the long term fluoride stability in a polyethylene glycol humectant system alone, without adversely affecting the cosmetic stability of the dentifrice. Accordingly, the glycerine component herein functions as, and is used as a chemical stabilizer for the fluoride ingredient.

The ability of quaternary ammonium compounds to inhibit the formulation of dental plaque is well documented. These compounds, however, present a problem when formulated in a dentifrice in that they are deactivated by traditional anionic surfactants such as sodium lauryl sulfate. Stable, clinically effective dental formulations have been made with quaternary ammonium compounds and nonionic surfactants, but these formulations are very poor foamers and result in inferior products. Compositions containing antiplaque quaternary ammonium compounds and nonionic surfactants are disclosed in U.S. Pat. No. 4,080,441, No. 4,110,429, No. 4,118,472, No. 4,118,473, No. 4,118,475, No. 4,118,476, and British Pat. No. 1,573,356.

U.S. Pat. No. 4,161,518 discloses a dentifrice composition for inhibiting plaque formation containing 0.05-1% by weight of a quaternary ammonium organosiloxane as the active antibacterial agent in a suitable vehicle containing suitable polishing agents, fluoride compounds, anionic surfactants, flavoring and sweetening agents, thickening agents such as a carboxymethylcellulose, humectants such as glycerin, sorbitol and other polyhydric alcohols.

U.S. Pat. No. 3,988,435 discloses a pharmaceutical compositions including a dentifrice containing a quaternary ammonium dihydrochalcone glucoside as the antibacterial agent having a sweet taste, as well as abrasives, surfactants including nonionics and "derivatives of fatty amines with betaine structures," swelling, gelling or thickening agents such as hydroxyalkylcellulose particularly hydroxyethylcellulose, polyethylene glycols, polypropylene glycols, etc., humectants such as sorbitol, mannitol, glycerin, propylene glycol, colorants, and flavors.

All of aforesaid cited patents simply list the conventional additives useful in dentifrice compositions. There is no disclosure of the use of the betaine as the exclusive surfactant in the production of a high foaming dentifrice. There is also no disclosure nor recognition of the necessity to limit the humectant to polyethylene glycol and/or sorbitol, and the thickening agent to nonionic gums such as hydroxyethylcellulose, in order to obtain a cosmetically stable dentifrice in a betainequat system. There is also no disclosure of the use of a small amount of glycerin to chemically stabilize the fluoride content without adversely affecting the cosmetic stability of the quaternary-betaine system.

U.S. Pat. No. 4,363,795 and its counterpart International Patent Publication No. WO 80/00057 to Wahlstam disclose a cleaning agent for dentine surfaces containing a quaternary ammonium compound, an ampholytic tenside which may be an imidazoline or a betaine and a sequestering agent of the aminocarboxylic acid type which has a synergistic effect as to the antibacterial properties of the treating solution. All the examples are in the form of cleaning solution. There is no mention of dental creams, nor the use of humectants and thickening agents, nor the use of small amounts of glycerin to stabilize the fluoride content.

U.S. Pat. No. 4,130,637 discloses a specific group of betaine compound, or a mixture of said betaine and its corresponding carboxylic acid quaternary ammonium salt in a 9:1 ratio, as non-staining antimicrobial antiplaque agents in a dentifrice vehicle containing the aforelisted conventional humectants and gelling agents, and a nonionic surfactant. This patent fails to disclose the necessity of using a betaine surfactant exclusively, the specific nonionic gelling agent hydroxyethylcellulose, the specific humectant polyethylene glycol, and/or sorbitol, and a small amount of glycerin, at least 1% and up to a maximum of 10% and preferably 5% by weight, to chemically stabilize the fluoride-containing compound, in order to obtain a stable, high foaming quaternary-containing antiplaque dentifrice.

U.S. Pat. Nos. 4,117,107 and 4,117,108 also disclose a specific group of betaine compounds and their salts as antiplaque agents in a dentifrice vehicle containing the conventional humectants and gelling agents, as well as anionic/nonionic surfactants. There is no disclosure of an antibacterial quaternary ammonium compound, a fluoride, and a betaine surfactant exclusively. There is also no recognition of the specificity of humectant and gelling agent and the exclusion of anionic/nonionic surfactants in a quaternary-betaine system, which is necessary in order to obtain a stable high foaming antiplaque dentifrice, nor the need for a small amount of glycerin to chemically stabilize the fluoride-containing compound.

None of the above cited prior art discloses a cosmetically-stable antiplaque dentifrice with improved foaming and improved fluoride stability containing as the essential ingredients a cationic quaternary antiplaque compound, a zwitterionic betaine surfactant, a humectant compatible with the cationic antiplaque agent selected from the group consisting of polyethylene glycol and sorbitol, the nonionic gelling agent hydroxyethylcellulose, a fluoride-providing compound, and about 1-10% glycerin to stabilize said fluoride compound, in an aqueous vehicle containing a dental abrasive.

SUMMARY OF THE INVENTION

It has now been found that dental cream formulations containing antiplaque quaternary ammonium compounds and fluoride-containing compounds may be stabilized and provide better foaming when betaine type surfactants replace the traditional anionic and nonionic surfactants. Humectants such as polyethylene glycol and sorbitol must replace the conventional glycerin for better cosmetic stability of the product. However, a small amount of glycerin is used to chemically stabilize the fluoride-containing compound. Nonionic gums such as hydroxyethylcellulose replace the anionic carboxymethylcellulose gelling agent which also has the potential to deactivate the quaternary compound.

Accordingly, a primary object of the present invention is to provide a better foaming antiplaque dentifrice based on quaternary active ingredients by the incorporation of a zwitterionic betaine surfactant as the foaming agent.

Another object of the present invention is to provide a cosmetically stable foaming antiplaque dentifrice containing polyethylene glycol and/or sorbitol, as humectant which is compatible with the betaine and the quaternary active ingredients.

Still another object of this invention is to provide a stable foaming antiplaque dentifrice containing the nonionic gum, hydroxyethylcellulose, as gelling agent to stabilize the betaine-quat system and to prevent deactivation of the quaternary active ingredient by the anionic sites of carboxymethylcellulose.

Another object of this invention is to provide a cosmetically (physical) and chemically stable foaming antiplaque dentifrice containing a fluoride-providing compound and 1-10% by weight of glycerin as stabilizing agent for the fluoride-providing compound without adversely affecting cosmetic stability of the dentifrice.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel stable foaming antiplaque dentifrice of this invention comprises a quaternary ammonium antiplaque compound, a zwitterionic betaine surfactant, a humectant selected from the group consisting of polyethylene glycol, sorbitol, and mixtures thereof, a nonionic gelling agent such as hydroxyethylcellulose, a fluoride-providing compound, and 1-10% by weight of glycerin as fluoride stabilizer in a polyethylene glycol humectant, in an aqueous vehicle containing a dental abrasive.

More specifically, present invention relates to a stable antiplaque dentifrice formulation with improved foaming and improved fluoride stability, comprising an effective antimicrobial amount of a quaternary ammonium compound, about 1.5-2% by weight betaine, about 20-30% by weight humectant selected from the group consisting of polyethylene glycol, sorbitol and mixtures thereof, about 0.5-2% by weight of hydroxyethylcellulose, about 0.05-2% by weight of a fluoride-providing compound, and preferably 5-7% by weight of glycerin stabilizer, in an aqueous vehicle containing about 40-60% water-insoluble dental abrasive.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2, pp. 632-635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial antiplaque quaternary ammonium compounds is benzethonium chloride, also known as Hyamine 1622 or diisobutylphenoxyethoxyethyl dimethyl benzyl ammonium chloride, and cetyl pyridinium chloride. In an oral preparation this material is highly effective in promoting oral hygiene by reducing formation of dental plaque and calculus, which is generally accompanied by a reduction in periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino,1,3-bis (2-ethylhexyl)-5-methyl hexa hydro-pyrimidine are typical quaternary ammonium antibacterial agents.

The dentifrice formulation of present invention contains an effective amount of the antiplaque quaternary ammonium compound, preferably about 0.01-5%, and most preferably 0.025-1% by weight of the composition.

The ability of quaternary ammonium compounds to inhibit the formation of dental plaque is well known. However, they are deactivated by the anionic surfactants such as sodium lauryl sulfate conventionally used in dentifrice formulations. The substitution of nonionic surfactants for the anionic surfactants eliminates the deactivation problem but results in products with poor foaming.

The incorporation of betaine surfactants into antiplaque dental formulations based on quaternary active ingredients improves the foaming of these formulations without deactivating the quaternary.

The betaine component of present dentifrice composition has the general formula:

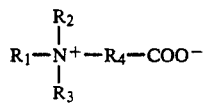

wherein $R_1$ is an alkyl group having 10 to about 20 carbon atoms, preferably 12 to 16 carbon atoms or the amido radical:

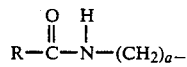

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyl dimethyl betaines include decyl betaine or 2-(N-decyl-N,N-dimethylammonio) acetate, coco betaine or 2-(N-coco-N,N-dimethylammonio) acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like.

The betaines, which are zwitterionic materials, function as a foaming agent in the quaternary-containing dentifrice compositions. They act cationically over a wide pH range but do not deactivate the quaternary antimicrobial activity. This is shown by in vitro tests using wool swatches, which simulate human skin and oral tissue, as the absorptive material in the Red Stain test, J. Soc. Cosmet, Chem. 31, 271–278 (September, October 1980). Wool has the same type of absorptive properties as oral tissue due to similar isoelectric and isoionic points.

Using the Red 80 Dye Test, the following experiment illustrates that the betaine surfactant doesn't deactivate the quaternary. The Red 80 Stain Test was performed using a solution of cocoamidopropyl betaine alone, benzethonium chloride alone, and a mixture of cocoamidopropylbetaine and benzethonium chloride. The degree of staining of the wool swatches treated with benzethonium chloride alone and the mixture of benzethonium chloride and betaine was nearly equal, and both were stained darker than the cocoamidopropyl betaine treated swatch. This indicates that benzethonium chloride is a "stronger" cationic compound than the betaine i.e. it has a greater attraction to the wool than the betaine, indicating that the betaine doesn't deactivate the benzethonium chloride.

However, wool swatches treated with a mixture of benzethonium chloride and the anionic surfactant, sodium lauryl sulfate, exhibits no staining (no red color retention) indicating complete deactivation of the benzethonium chloride by the anionic surfactant.

The degree of staining of the wool swatches treated with a mixture of benzethonium chloride and the nonionic surfactant, polyoxyethylene (20 moles ethylene oxide) sorbitan di-iso stearate, was substantially equal to that of the benzethonium chloride alone. This indicates that the benzethonium is not deactivated by the nonionic surfactant.

In addition to the non-interference exhibited by the betaines with the quaternary activity, laboratory foam tests have shown that formulations containing both the quat and the betaine, foam 2–3 times better than the nonionic/quat formulations. The foam index for nonionic/quat compositions is about 20, whereas the foam index for betaine/quat compositions is about 40–60. The foam test used herein comprises placing 1 gram of the test dentifrice in 10 ml of 175 PPM water at 90° F. in a 100 ml graduated cylinder, shaking for 15 seconds and reading the foam height.

The zwitterionic betaines are completely compatible with the quaternary antimicrobial antiplaque agents, and impart detersive and improved foaming properties to the quaternary-containing dentifrice composition without deactivating the antimicrobial properties thereof. The amount of betaine effective in the production of improved foaming may be varied from about 1.5–2% active ingredient by weight of the total formulation. Greater amounts of betaine adversely affect the taste of the dentifrice.

The fluoride-providing compounds, which are essential ingredients in present dentifrice, are characterized by their ability to release fluoride ions in water and by substantial freedom from reaction with other compounds of the dentifrice. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluoride-providing compound is dependent to some extent, upon the type of compound, its solubility, and the dentifrice, but it must be a nontoxic amount. In a solid oral preparation, such as a toothpaste or dental cream, an amount of such compound which releases a maximum of 1% by weight of the preparation is considered satisfactory. Any suitable minimum amount of such compound may be used, but it is preferable to employ sufficient compound to release from 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.5% to 1%. In the case of sodium monofluorophosphate, the compound may be present in an amount up to 7.6% by weight, more typically 0.76%.

Cosmetic problems of stability are incurred with all zwitterionic-containing dentifrices, such as crimp leakage of flavor. The flavor oozes and is not solubilized in the zwitterionic surfactant.

Accordingly, in order to effect cosmetic stability of the betaine system, a specific group of humectants which includes polyethylene glycol, sorbitol or mixtures thereof must be used. Glycerin and/or propylene glycol alone provide insufficient cosmetic stability to the betaine system. The humectant constitutes 10–30% by weight and preferably 10–25%, and is selected from the group consisting of polyethylene glycol, sorbitol and mixtures thereof.

However, the use of small amounts of glycerin, at least 1% and up to a maximum of 10%, and preferably 5–7% by weight, in present formulations containing a fluoride, markedly improves long term fluoride stability. Based on the three week results of the 120° F. aging study, 5% glycerin improves the fluoride stability 25% without adversely affecting cosmetic stability. The mechanistic reason why the presence of some glycerin improves the fluoride stability is unclear. Fluoride stability data after 12 weeks at 100° F. further confirms the significant improvement with the use of small amounts of glycerin in the dentifrice. Table I clearly shows this improved fluoride stability in a polyethylene glycol humectant system.

TABLE I

| Glycerine: Polyethylene Glycol | Soluble Fluoride | | | | |
|---|---|---|---|---|---|
| | Initial | 3 wks @ 100° | 6 wks @ 100° | 9 wks @ 100° | 12 wks @ 100° |
| 0:20 | 0.093 | 0.077 | 0.068 | 0.063 | 0.057 |
| 1:19 | 0.088 | 0.081 | 0.074 | 0.066 | 0.066 |
| 3:17 | 0.093 | 0.082 | 0.074 | 0.069 | 0.067 |
| 5:15 | 0.093 | 0.081 | 0.077 | 0.071 | 0.070 |
| 10:10 | 0.094 | 0.086 | 0.083 | 0.080 | 0.077 |

It has also been found that increase in the glycerin content results in decreases in pH as shown in Table II.

TABLE II

| Glycerin:Polyethylene Glycol | pH 9 wks @ 120° |
|---|---|
| 0:20 | 9.8 |
| 1:19 | 9.7 |
| 3:17 | 9.4 |
| 5:15 | 9.4 |
| 10:10 | 8.9 |

Another essential ingredient in present dentifrice is a gelling agent which is a nonionic gum, in an amount up to 5% by weight and preferably about 0.5–2%. It has been found that large organic anionic molecules such as carboxymethylcellulose have the potential to deactivate the quaternary antibacterial activity. Accordingly, hydroxyethylcellulose, which is a nonionic organic molecule, effects a stable pituitous gel in the betaine-quat system of present invention, and is the preferred gelling agent. Other nonionic gelling agents may be used such as hydroxymethylcellulose, and the like.

It has been found that only by utilizing the specific combination of ingredients of betaine, polyethylene glycol and/or sorbitol humectant, nonionic gelling agent, and a small amount of glycerin, can a stable fluoride-containing antiplaque dentifrice with improved foaming and improved fluoride stability based on the quaternary antibacterial compounds, be obtained.

The dentifrice of this invention, which is a toothpaste or dental cream, contains conventional water-insoluble polishing materials or dental abrasives, in amounts from about 20–75% and preferably about 40–60% by weight of the total formulation. Suitable examples of dental abrasives or polishing materials include sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof.

The dentifrice of this invention may also contain conventional additional ingredients such as coloring or whitening agents, preservatives, flavoring or sweetening materials, and ammoniated materials such as mono-ammonium glycyrrhizinate. These additional ingredients may each be added to the dentifrice in minimal amounts of up to 5% by weight, and preferably up to 1%, provided they do not interfere with the foaming, antiplaque and stability properties of the finished product.

The dentifrice of this invention is prepared by conventional methods of making toothpaste and/or dental creams. More specifically, a toothpaste may be prepared by forming a gel with hydroxyethylcellulose and water, adding thereto with mixing the powdered materials which includes the fluoride compound and humectant, followed by the addition with mixing of polishing agent and then the betaine and flavor, and tubing the final mixture.

In the practice of this invention to promote oral hygiene, the dentifrice according to this invention is applied regularly to dental enamel by brushing the teeth for 30–90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLE 1

| Ingredients | % |
|---|---|
| Hydroxyethylcellulose | 1.0 |
| Carbowax 600[1] | 20.0 |
| Na Saccharin | 0.2 |
| MFP[2] | 0.76 |
| CAB[3] (35% A.I.) | 3.5 |
| Dicalcium Phosphate | 49.0 |
| BZCl[4] | 0.5 |
| D.I. H$_2$O | 24.04 |
| Flavor | 1.0 |

[1]Polyethylene glycol, mol. weight 600
[2]Sodium monofluorophosphate
[3]Cocoamidopropyl betaine
[4]Benzethonium chloride The hydroxyethylcellulose and water are premixed for 10 minutes to form a gel. The powdered materials MFP, BZCl and saccharin, and the Carbowax humectant is added to the gel and mixed for 10 to 20 minutes. The gelled mixture is added to dicalcium phosphate and mixed for 20 minutes at speed 8 in the Ross agitator. The betaine and flavor is added to the mixture and mixed for 5 minutes at speed 6 in the Ross agitator. The resultant dental cream which is cosmetically attractive is tubed.

Aging tests performed on this product in lined tubes at room temperature, 40° F. and 100° F. for 9 weeks, and in unlined tubes at 120° F. for 9 weeks, exhibit excellent cosmetic stability.

EXAMPLE 2

| Ingredients | % |
|---|---|
| Hydroxyethylcellulose | 1.1 |
| Carbowax 600 | 20.0 |
| Na Saccharin | 0.2 |
| MFP | 0.76 |
| CAB (35% A.I.) | 5.7 |
| Dicalcium Phosphate | 46.8 |
| BZCl | 0.5 |
| H₂O | 24.04 |
| Flavor | 1.0 |

This dental cream is prepared in accordance with the procedure of Example 1. This product has a pH of 6.7 and a foam height of 55, but does not taste good.

EXAMPLE 3

| Ingredients | % |
|---|---|
| Hi Sweet peppermint | 1.0 |
| MAG[1] | 0.1 |
| BZCl | 0.5 |
| MFP | 0.76 |
| Na Saccharin | 0.2 |
| H₂O | 23.44 |
| PEG 600[2] | 20.0 |
| Natrosol[3] | 1.0 |
| Dicalcium phosphate | 49.0 |
| CAB (30% A.I.) | 4.0 |

[1] Monoammonium glycyrrhizinate
[2] Polyethylene glycol, molecular weight 600
[3] Hydroxyethylcellulose This dental cream is prepared according to the procedure of Example 1, except that the pH is adjusted to 8.5 with dilute NaOH for hydration purposes, after the polyethylene glycol is added to the gelled premix.

The resultant cream looks good, has a foam height of 38–40, and shows excellent stability using aging tests over a period of 12 weeks at 100° F. as well as at 140° F. in unlined tubes for 3 weeks.

EXAMPLE 4

Example 3 is repeated except that glycerin replaces the polyethylene glycol humectant. This product gives a foam height of 46, but shows trace separation in 3 days at 140° F. and a wetness and separation at the neck of the tube at 120° F. in 3 weeks. This product is cosmetically unstable.

EXAMPLE 5

| Ingredients | % |
|---|---|
| H₂O | 21.14 |
| Natrosol | 1.3 |
| Propylene glycol | 20.0 |
| Na Saccharin | 0.2 |
| BZCl | 0.5 |
| MAG | 0.1 |
| MFP | 0.76 |
| Dicalcium phosphate | 50.0 |
| CAB (30% A.I.) | 5.0 |
| Flavor | 1.0 |

This dental cream is prepared according to the procedure of Example 1 except that the propylene glycol humectant is mixed with the premix gel for only 10 minutes. The resulting product is good in appearance and foaming with a foam height of 44. However, it's instability is clearly evident by separation, wetness along the ribbon and clip leakage in 3 weeks at 8° F. and 40° F., and slight yellowing at 110° F. and 120° F. within 3 weeks.

EXAMPLE 6

| Ingredients | % |
|---|---|
| H₂O | 19.68 |
| Natrosol | 1.1 |
| Carbowax 600 | 20.0 |
| Na Saccharin | 0.2 |
| BZCl | 0.5 |
| MAG | 0.1 |
| MFP | 0.76 |
| Dicalcium phosphate | 50.0 |
| CAB (30% A.I.) | 6.66 |
| Flavor | 1.0 |

This dental cream is prepared according to the procedure of Example 1.

The resulting product is slightly thick but exhibits good foaming and stability.

EXAMPLE 7

| Ingredients | % |
|---|---|
| H₂O | 21.34 |
| Natrosol | 1.1 |
| Carbowax 600 | 20.0 |
| Na Saccharin | 0.2 |
| BZCl | 0.5 |
| MAG | 0.1 |
| MFP | 0.76 |
| $Ca_2P_2O_7$[1] | 50.0 |
| CAB (30% A.I.) | 5.0 |
| Flavor | 1.0 |

[1] Calcium pyrophosphate

This dental cream is prepared according to the procedure of Example 1.

The resulting cream is thick and grainy, which may be due to the coarseness of the calcium pyrophosphate dental abrasive.

EXAMPLE 8

| Ingredients | % |
|---|---|
| H₂O | 17.68 |
| Natrosol | 1.1 |
| Carbowax 600 | 20.0 |
| Na Saccharin | 0.2 |
| BZCl | 0.5 |
| MAG | 0.1 |
| MFP | 0.76 |
| Dicalcium phosphate dihydrate | 42.0 |
| Anhydrous Dicalcium phosphate | 10.0 |
| CAB (30% A.I.) | 6.66 |
| Flavor | 1.0 |

EXAMPLE 9

| Ingredients | % |
|---|---|
| Carbowax 600 | 20.0 |
| Natrosol | 1.1 |
| Na Saccharin | 0.2 |
| MAG | 0.1 |
| BZCl | 0.5 |
| H₂O | 17.68 |
| MFP | 0.76 |
| Hydrated Alumina | 42.0 |
| Calcined Alumina | 10.0 |

| Ingredients | % |
| --- | --- |
| CAB (30% A.I.) | 6.66 |
| Flavor | 1.0 |
| pH 8.3 | |

This product shows complete stability after aging for 9 weeks at oom temperature, 40° F., 100° F. and 120° F.

EXAMPLES 10 and 11

| Ingredients | Ex. 10 % | Ex. 11 % |
| --- | --- | --- |
| PEG 600 | 20.0 | 20.0 |
| Natrosol | 1.1 | 1.3 |
| Na Saccharin | 0.3 | 0.3 |
| Hydrated Alumina | 42.0 | 42.0 |
| Calcined Alumina | 10.0 | 10.0 |
| CAB (30% A.I.) | 5.0 | 5.0 |
| MFP | 0.76 | 0.76 |
| Flavor | 1.0 | 1.0 |
| H$_2$O D.I. | 19.27 | 18.64 |
| BZCl | 0.5 | 0.5 |
| Red 40 (1% solution) | 0.07 | 0.07 |

EXAMPLE 12

| Ingredients | % |
| --- | --- |
| Sorbitol 70% | 28.0 |
| Natrosol | 1.1 |
| Na Saccharin | 0.3 |
| BZCl | 0.5 |
| MFP | 0.76 |
| Alumina | 42.0 |
| Calcined Alumina | 10.0 |
| CAB (30% A.I.) | 5.0 |
| Flavor | 1.0 |
| H$_2$O | 11.34 |
| Initial pH 7.4 | |
| 3 weeks pH 7.5 | |
| 6 weeks pH 7.6 | |

This product exhibits complete stability at 8° F. and 40° F. for a period of 9 weeks but slight wet cap at 110° F. and 120° F. after 3–9 weeks. In addition to the good physical stability of this product, the active ingredient content (ionic fluoride and the benzethonium chloride) remains stable as evidenced by the substantially stable pH.

EXAMPLE 13

| Ingredients | % |
| --- | --- |
| H$_2$O | 21.14 |
| Natrosol | 1.3 |
| Sorbitol | 20.0 |
| Na Saccharin | 0.2 |
| BZCl | 0.5 |
| MAG | 0.1 |
| MFP | 0.76 |
| Dicalcium phosphate dihydrate | 50.0 |
| CAB (30% A.I.) | 5.0 |
| Flavor | 1.0 |

The resultant cream exhibits a foam height of 42 and no flavor separation after 9 weeks at 120° F. This product is completely stable at 8° F. and 40° F. for a period of 9 weeks, but exhibits traces of a wet cap at 110° F. and 120° F. after 3 to 9 weeks.

EXAMPLE 14

| Ingredients | % |
| --- | --- |
| Natrosol | 1.1 |
| Na Saccharin | 0.3 |
| BZCl | 0.5 |
| MFP | 0.76 |
| Carbowax 600 | 10.0 |
| Sorbitol (70%) | 10.0 |
| H$_2$O deionized | 19.34 |
| Hydrated Alumina | 10.0 |
| Calcined Alumina | 42.0 |
| Flavor | 1.0 |
| CAB (30% A.I.) | 5.0 |

EXAMPLE 15

| Ingredients | % |
| --- | --- |
| Natrosol | 1.1 |
| Na Saccharin | 0.3 |
| MFP | 0.76 |
| BZCl | 0.5 |
| Carbowax 600 | 15.0 |
| Sorbitol (70%) | 5.0 |
| H$_2$O | 19.34 |
| Hydrated Alumina | 42.0 |
| Calcined Alumina | 10.0 |
| Flavor | 1.0 |
| CAB (30% A.I.) | 5.0 |

This product which contains 5% sorbitol, exhibits 84% soluble fluoride recovery at 12 weeks at 100° F., as compared to 61% fluoride recovery (acceptable level) for the polyethylene glycol humectant system alone under the same conditions, e.g. Examples 1 through 11 and 20. This indicates that the presence of sorbitol, in amounts as low as 5% (70% A.I.), provides superior fluoride stability, similarly to the presence of small amounts of glycerin (Examples 16–19) in a polyethylene glycol humectant system.

EXAMPLES 16–20

| Ingredients | % Ex. 16 | % Ex. 17 | % Ex. 18 | % Ex. 19 | % Ex. 20 |
| --- | --- | --- | --- | --- | --- |
| Polyethylene Glycol (Carbowax 600) | 15 | 17 | 19 | 10 | 20 |
| Glycerin | 5 | 3 | 1 | 10 | 0 |
| Hydroxyethyl Cellulose | 1.10 | 3 | 1 | 10 | 0 |
| Sodium Monofluorophosphate | 0.76 | 3 | 1 | 10 | 0 |
| Sodium Saccharin | 0.30 | 3 | 1 | 10 | 0 |
| Benzethonium chloride | 0.50 | 3 | 1 | 10 | 0 |
| Hydrated Alumina | 42 | 3 | 1 | 10 | 0 |
| Calcined Alumina | 10 | 3 | 1 | 10 | 0 |
| CAB (30%) | 5 | 3 | 1 | 10 | 0 |
| Flavor | 1 | 3 | 1 | 10 | 0 |
| Water | 19.34 | 3 | 1 | 10 | 0 |
| Fl$^-$ content* | 0.07 | 0.067 | 0.066 | 0.077 | 0.057 |

*Chemical stability of the above formulations after accelerated aging for 12 weeks at 100° F. as determined by the percentage of Fl$^-$ content All the above formulations are effective against plaque related bacteria while possessing improved foaming characteristics, cosmetic stability and chemical stability. The presence of a small amount of glycerin, as low as 1% by weight, enhances the chemical stability of the fluoride in the dentifrice over the acceptable fluoride stability in the absence of glycerin (Example 20).

Variations in the above formulations may be made. For example, other betaines such as lauramidopropyl betaine, coco betaine and the like may be substituted for the cocoamidopropyl betaine in the examples. Similarly, other abrasives may be substituted for the specific abrasives in the examples. Likewise, other fluoride-containing compounds such as sodium fluoride, potassium fluoride, etc. may be substituted for the sodium monofluorophosphate in the specific examples.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable antiplaque dentifrice with improved foaming and improved fluoride stability, comprising an effective amount of an antiplaque quaternary ammonium compound, at least 1.5% betaine surfactant by weight, a humectant selected from the group consisting of polyethylene glycol, sorbitol and mixtures thereof, a nonionic gelling agent, a fluoride-providing compound, in an aqueous vehicle containing a dental abrasive.

2. The dentifrice according to claim 1, wherein the betaine content constitutes about 1.5-2% by weight of the formulation.

3. The dentifrice of claim 2, wherein the nonionic gelling agent is hydroxyethylcellulose in amounts of about 0.5-2% by weight.

4. The dentifrice according to claim 3, containing about 20-30% by weight of polyethylene glycol having an average molecular weight of 600 and 1-10% glycerine by weight as fluoride stabilizer.

5. The dentifrice according to claim 3, containing about 20-30% by weight of sorbitol.

6. The dentifrice according to claim 1, containing about 40-60% by weight of a water-insoluble dental abrasive.

7. The dentifrice according to claim 6, wherein the dental abrasive is dicalcium phosphate.

8. The dentifrice according to claim 3, wherein the antiplaque agent is benzethonium chloride in an amount of about 0.01-5% by weight.

9. The dentifrice according to claim 6, wherein the dentifrice is a mixture of calcined alumina and hydrated alumina.

10. The dentifrice according to claim 1, wherein the fluoride-providing compound constitutes 0.05-2% by weight of the dentifrice.

11. The dentifrice according to claim 10, wherein the fluoride-providing compound is sodium monofluorophosphate.

12. The dentifrice of claim 2, wherein the betaine is cocoamidopropyl betaine.

13. The dentifrice according to claim 1, which is free of nonionic and anionic surfactants.

14. The dentifrice according to claim 6, wherein the abrasive is dicalcium phosphate.

15. The dentifrice according to claim 6, wherein the abrasive is alumina.

16. The dentifrice according to claim 15, wherein the abrasive is a mixture of hydrated alumina and calcined alumina.

17. The dentifrice according to claim 3, wherein the humectant comprises about 20-30% by weight of a mixture of sorbitol and polyethylene glycol.

* * * * *